United States Patent
Jeffrey

(10) Patent No.: US 10,945,650 B2
(45) Date of Patent: Mar. 16, 2021

(54) MEDICAL CONNECTOR

(71) Applicant: MEDICAL DEVICE CREATIONS LIMITED, Liverpool (GB)

(72) Inventor: Peter Jeffrey, Liverpool (GB)

(73) Assignee: Medical Device Creations Limited, Liverpool (GB)

( * ) Notice: Subject to any disclaimer, the term of this patent is extended or adjusted under 35 U.S.C. 154(b) by 308 days.

(21) Appl. No.: 15/577,976

(22) PCT Filed: May 27, 2016

(86) PCT No.: PCT/GB2016/051572
§ 371 (c)(1),
(2) Date: Nov. 29, 2017

(87) PCT Pub. No.: WO2016/193693
PCT Pub. Date: Dec. 8, 2016

(65) Prior Publication Data
US 2018/0289303 A1 Oct. 11, 2018

(30) Foreign Application Priority Data
May 29, 2015 (GB) .................................... 1509262

(51) Int. Cl.
*A61B 5/15* (2006.01)
*A61M 39/10* (2006.01)
(Continued)

(52) U.S. Cl.
CPC .... *A61B 5/150221* (2013.01); *A61B 5/15003* (2013.01); *A61B 5/150992* (2013.01);
(Continued)

(58) Field of Classification Search
CPC .................. A61M 39/10; A61M 39/24; A61M 2039/1072; A61M 39/2493;
(Continued)

(56) References Cited

U.S. PATENT DOCUMENTS 5,048,537 A * 9/1991 Messinger ........... A61B 5/0215
600/486
5,148,811 A 9/1992 Messinger
(Continued)

FOREIGN PATENT DOCUMENTS

CN 103961793 A 8/2014
EP 2282806 B1 5/2013
(Continued)

OTHER PUBLICATIONS

International Search Report, dated Nov. 21, 2016 (PCT/GB2016/051572).

*Primary Examiner* — Nathan R Price
*Assistant Examiner* — Dung T Ulsh
(74) *Attorney, Agent, or Firm* — Robert L. Stearns; Dickinson Wright, PLLC

(57) ABSTRACT

Inside a connector body (112, 114; 300) of a medical connector providing a fluid flow conduit, a one-way valve (118) is fitted directly into one end of a stop valve (116) in a manner providing a fluid tight seal between these valves. The stop valve (116) prevents fluid flowing out of the end (111; 311) of the connector body (112, 114; 300) unless a complementary end of a separate device (not shown), typically a Luer lock connector, engages the end of the connector body and opens the stop valve (116). To facilitate manufacture and assembly, the one-way valve (118) and the stop valve (116) can be formed as parts of a single piece of elastomeric material, the parts being hingedly connected so that the one-way valve part (118) can be folded over to be fitted directly into the end of the stop valve part (116). A further possibility, also applicable when only a stop valve (116) is provided, is that the connector body (300) may be formed in one piece with a folding, snap fit closure (312).

10 Claims, 7 Drawing Sheets

(51) Int. Cl.
   *A61M 39/24* (2006.01)
   *A61M 39/22* (2006.01)
   *A61M 39/26* (2006.01)
(52) U.S. Cl.
   CPC ............ *A61M 39/10* (2013.01); *A61M 39/24* (2013.01); *A61M 2039/1072* (2013.01); *A61M 2039/229* (2013.01); *A61M 2039/2493* (2013.01); *A61M 2039/267* (2013.01); *A61M 2205/584* (2013.01); *A61M 2205/70* (2013.01); *A61M 2207/00* (2013.01)
(58) Field of Classification Search
   CPC ...... A61M 2039/267; A61M 2039/229; A61B 5/150221; A61B 5/150992; A61B 5/15003
   See application file for complete search history.

(56) References Cited

U.S. PATENT DOCUMENTS

| | | |
|---|---|---|
| 2004/0171993 A1 | 9/2004 | Bonaldo |
| 2005/0228346 A1* | 10/2005 | Goode .............. A61M 39/0606 604/164.07 |
| 2007/0225648 A1 | 9/2007 | Winsor et al. |
| 2008/0067462 A1 | 3/2008 | Miller et al. |
| 2010/0249723 A1* | 9/2010 | Fangrow, Jr. ...... A61M 39/1011 604/247 |
| 2011/0098598 A1* | 4/2011 | Young ................... A61M 39/24 600/573 |
| 2011/0319859 A1 | 12/2011 | Zeytoonian et al. |
| 2014/0261082 A1* | 9/2014 | Anderson ........... B01F 13/0023 106/287.35 |
| 2014/0276455 A1* | 9/2014 | Yeh ....................... A61M 39/24 604/247 |
| 2016/0114128 A1* | 4/2016 | Lancette ............ A61M 39/1011 604/535 |
| 2017/0136151 A1* | 5/2017 | Anderson ............. A61J 1/2096 |

FOREIGN PATENT DOCUMENTS

| | | |
|---|---|---|
| EP | 2777757 A1 | 9/2014 |
| GB | 2458572 A | 9/2009 |
| WO | 9515194 A1 | 6/1995 |

\* cited by examiner

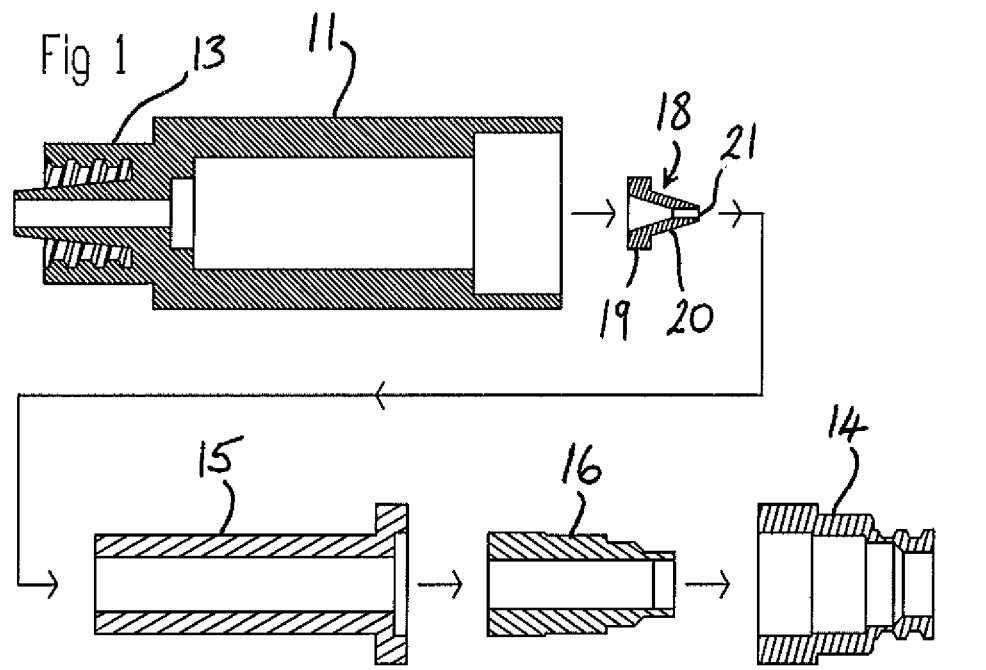
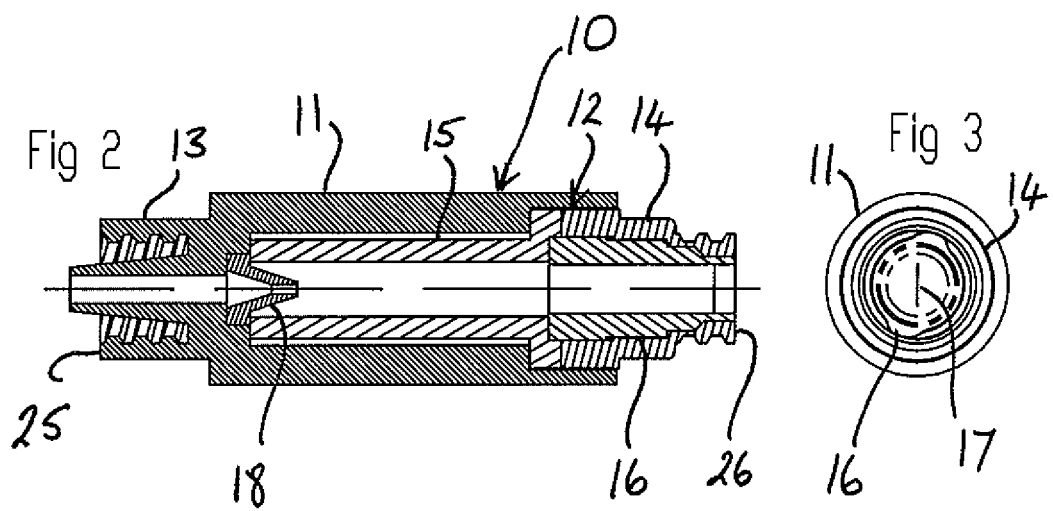

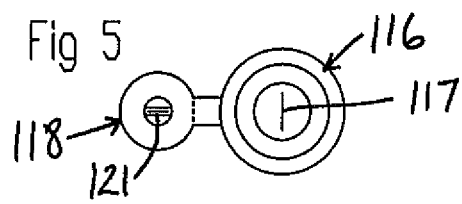
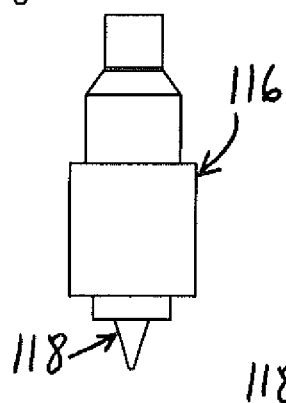
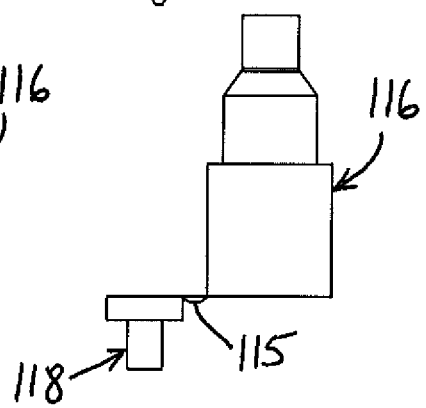
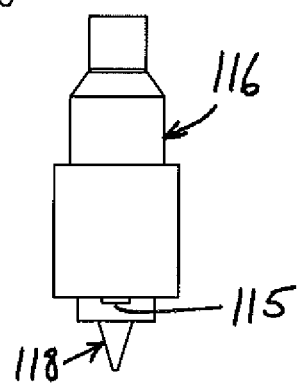
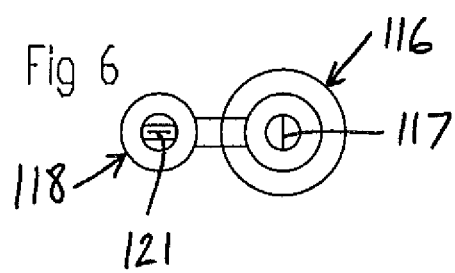

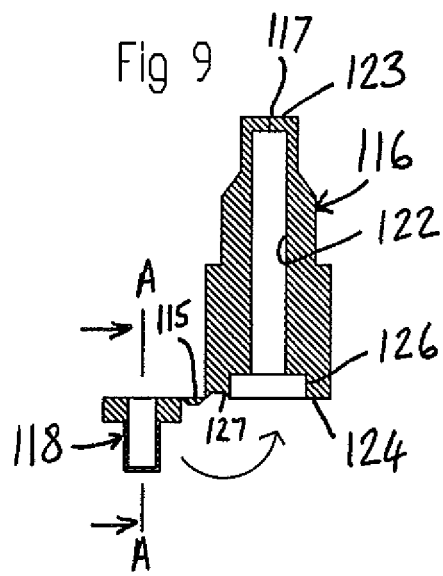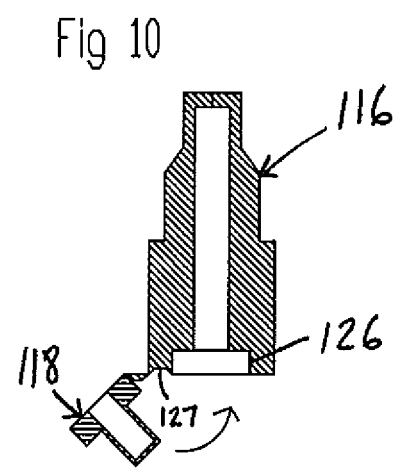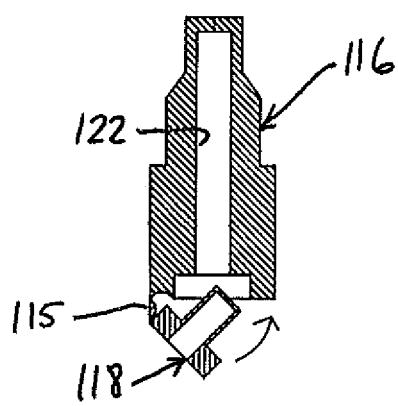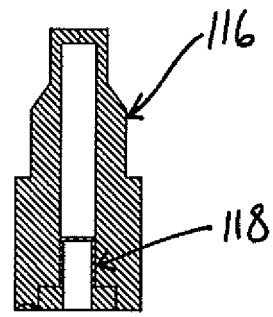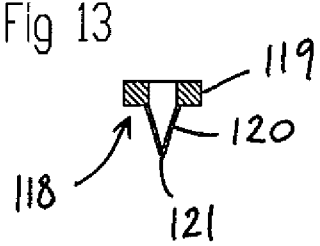

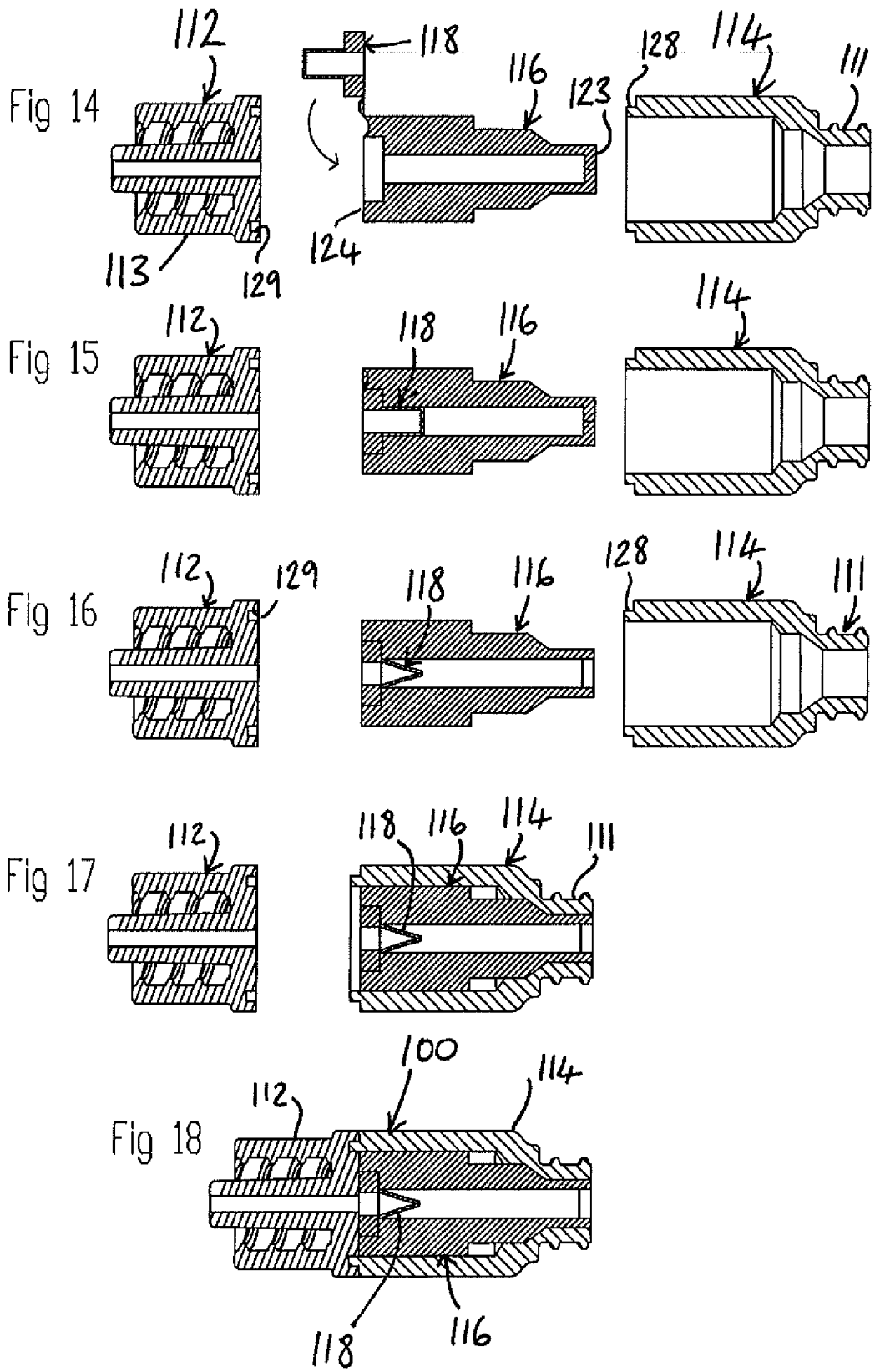

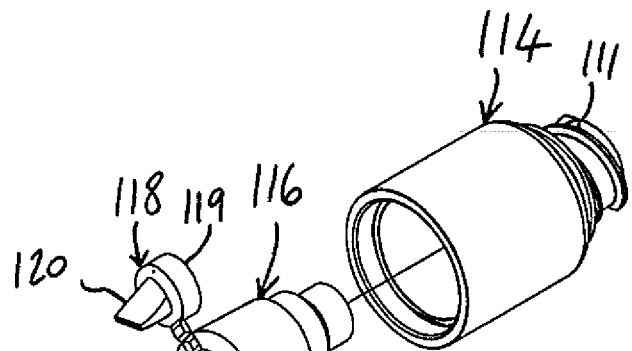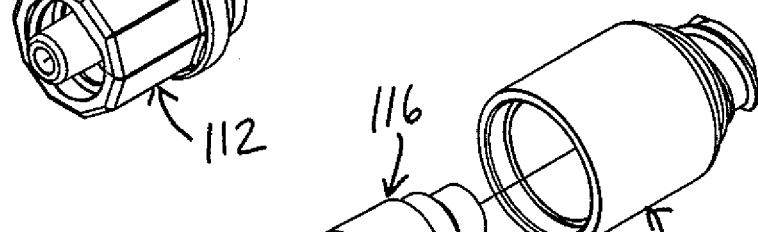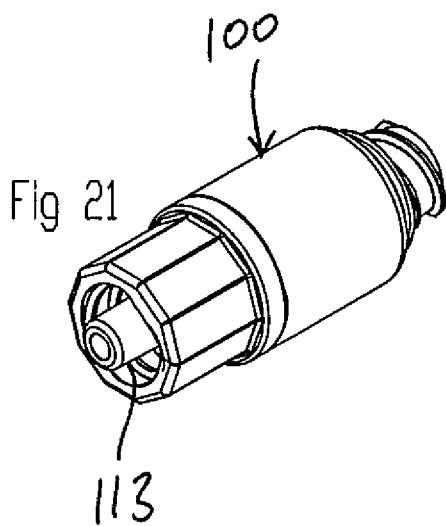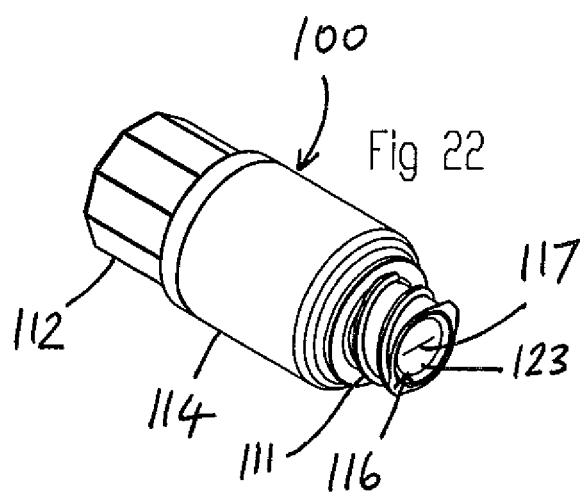

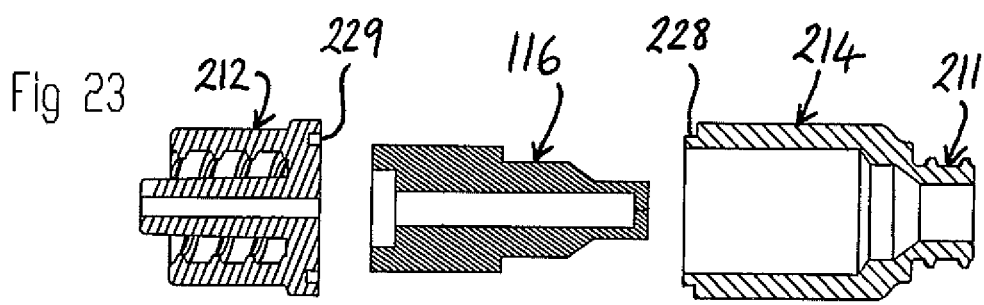
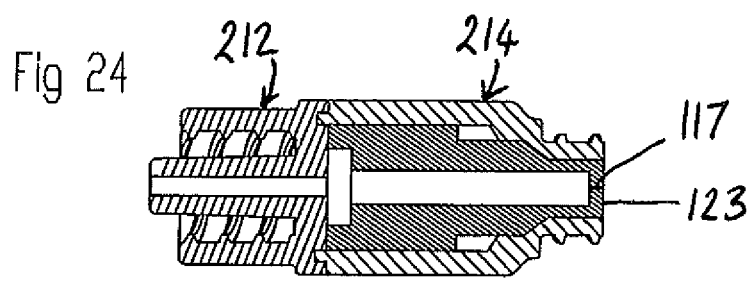

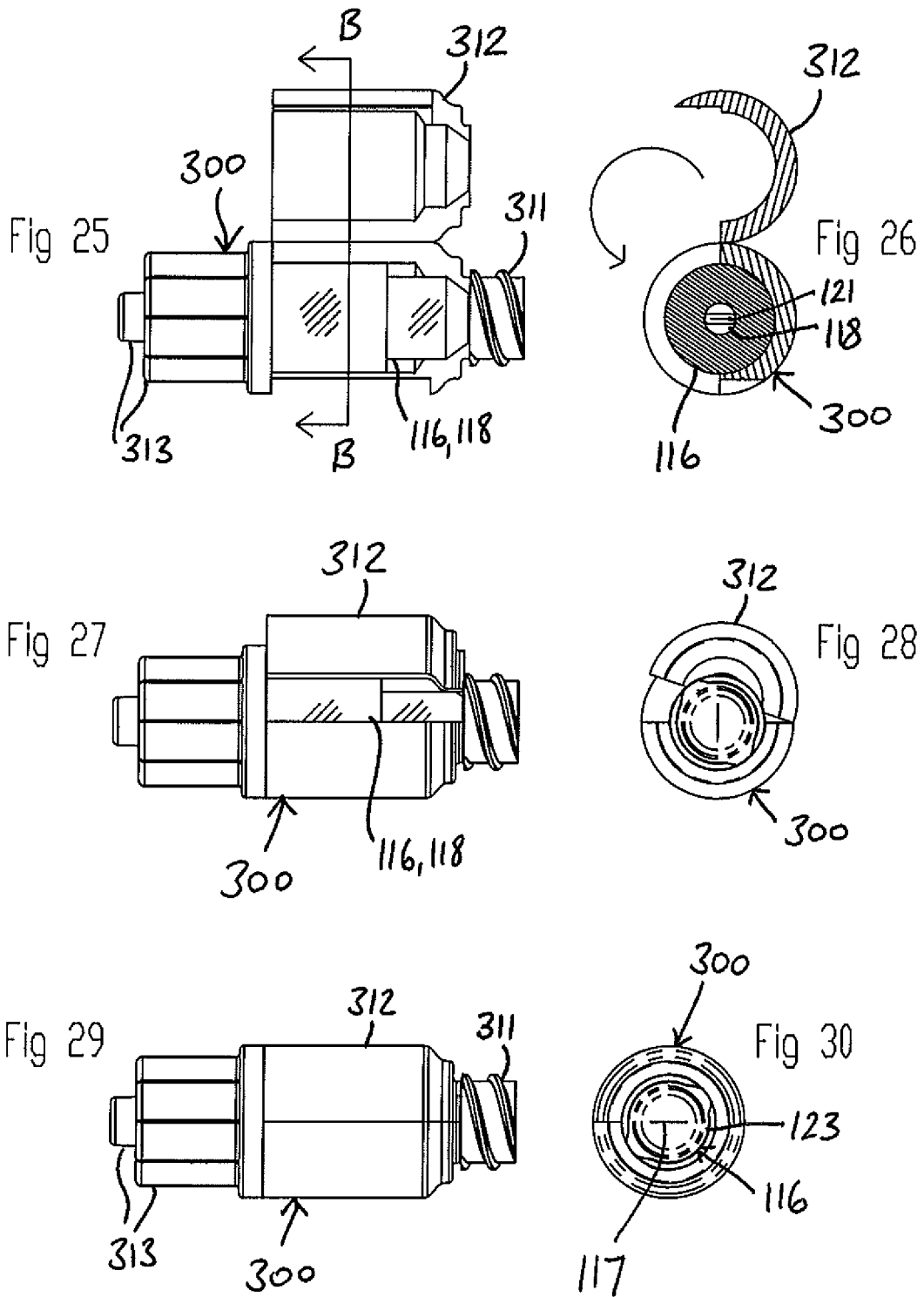

MEDICAL CONNECTOR

BACKGROUND

1. Technical Field

This invention relates to a connector for medical purposes for use, particularly but not exclusively, in withdrawing samples of a body fluid.

2. Related Art

In medical practice there are several circumstances where fluid samples are required to be taken from blood vessels or body cavities, but where accidental injection of substances, such as pharmaceuticals, glucose or air is undesirable, detrimental or could be fatal. One instance is where blood samples are required to be withdrawn from the arterial system. This is typically done using a three-way tap which allows for sampling through one port and for flushing with saline through another port. Another instance is where a fluid sample has to be taken from the subarachnoid space of the brain. There are also a number of medical procedures requiring one-way flow of body fluid where it would be beneficial to prevent the flow of body fluid in the opposite, "wrong" direction. For example, cardiopulmonary bypass equipment requires blood to flow from the arterial system out of the body and back into the body via the venous system and it would be beneficial to prevent the possibility of reverse direction flow which might result from user error.

EP 2282806 discloses a sampling connector for use as an adapter for a three-way tap arterial blood sampling device, which connector incorporates a one-way valve allowing fluid to flow through the connector in one direction only. This connector is attached onto the sampling port of the three-way tap so that fluid can only flow in a direction from the body and out of the sampling port. The connector is also disclosed as including a stop valve which prevents fluid flowing out of the outer end of the connector body (namely the end remote from the sampling port of the three-way tap) unless a complementary end of a separate device engages the outer end and opens the stop valve. This prevents leakage of body fluid through the tap and the connector when a separate device, such as a sample collecting syringe, is not attached to the connector.

It should be noted that connector devices which incorporate only a stop valve having aforesaid function, namely preventing fluid from flowing out of one end of the connector body unless a complementary end of a separate device engages that end and opens the stop valve, are commercially available and are routinely used in respect of standardised medical equipment, particularly for connection to patient fluid lines. These known connector devices typically have a male end formed as a Luer slip connector or Luer lock connector and a female end comprising a female Luer connector, and the stop valve is mounted adjacent the female end to provide a needleless entry port, into which a complementary male Luer connector is inserted in order to open that port. Such connector devices are, for example, provided on bags of saline or other fluid for medical purposes for standardised connection to patient fluid supply lines provided with male Luer lock connection means.

While EP 2282806 discloses desirable inclusion of a one-way valve and a stop valve in an adapter for arterial blood sampling by way of a three-way tap, the present invention is concerned with manufacture of a connector, for this purpose and other purposes, with the objective of ease of assembly and quality assurance, hence highly cost-effective supply of reliable medical connectors as required by modern medical services.

SUMMARY OF THE INVENTION

According to an aspect of the invention, there is provided a medical connector comprising a connector body having first and second apertures in fluid communication via a fluid flow conduit, a one-way valve disposed in the body to allow fluid to flow from the first aperture, through the fluid flow conduit and out of the second aperture, but not to allow fluid to flow from the second aperture and through the fluid flow conduit to the first aperture, and a stop valve which prevents fluid flowing out of the second aperture of the connector body unless a complementary end of a separate device engages the second aperture and opens the stop valve, wherein the connector body, the one-way valve is fitted directly into an end of the stop valve part in a manner providing a fluid tight seal between these valve parts.

In certain embodiments, the one-way valve and the stop valve may be formed as parts of a single piece of elastomeric material, said parts may be hingedly connected such that the one-way valve part is folded over and fitted directly into the end of the stop valve part. Optionally, the end of the stop valve into which the one-way valve is fitted is formed with a recess and a periphery of the one-way valve seats in that recess. The recess may be configured so that the one-way valve is fully counter sunk into the end of the stop valve.

In certain embodiments, the one-way valve part and the stop valve part may be additionally connected by a strap portion of the elastomeric material, said strap may be folded over such that the one-way valve fits into the end of the stop valve.

The one-way valve may be a duck bill valve. The stop valve may be a swabable entry port valve. The connector body may be formed of only two body parts. The connector body may be formed in one piece with a folding, snap fit closure.

According to a further aspect of the invention, there is provided a medical connector comprising a connector body having first and second apertures in fluid communication via a fluid flow conduit, and a stop valve disposed in the body adjacent the second aperture, which stop valve prevents fluid flowing out of the second aperture of the connector body unless a complementary end of a separate device engages the second aperture and opens the stop valve, wherein the connector body is formed in one piece with a folding, snap fit closure.

In certain embodiments, according to either above mentioned aspects of the invention, the first aperture may be within a male end of the connector which is configured as a male Luer lock connector portion. Additionally or alternatively, the second aperture may be within a female end of the connector which is configured as a female Luer lock connector portion and provides a swabable entry port for attachment of a complementary needleless device.

According to a further aspect of the invention, there is provided a three-way tap arterial blood sampling device incorporating the sampling connector according to the either of the medical devices described above.

According to a further aspect of the invention, there is provided a method of producing a medical connector, e.g. as described above, comprising the steps of: forming a one-way valve and a stop valve; forming parts of a connector body; mounting the stop valve and the one-way valve inside the body parts so that the one-way valve fits directly into one end of the stop valve; and attaching the body parts together.

According to a further aspect of the invention, there is provide a method of producing a medical connector, e.g. as described above, comprising the steps of: forming a one-way valve and a stop valve; forming a connector body in one piece with a folding, snap fit closure; mounting the stop valve and the one-way valve inside the connector body so that the one-way valve fits directly into one end of the stop valve; and closing the connector body by folding and snap fitting the closure.

In certain embodiments, according to either of the methods described above, the one-way valve and the stop valve may be formed as parts of a single piece of elastomeric material, said parts may be hingedly connected, and/or the mounting of the stop valve and the one-way valve inside the connector body may include folding the one-way valve part over relative to the stop valve part.

In certain embodiments, the connector body may be formed from only two parts and/or the assembled valve parts may be fitted into one part of the body and/or the other part of the body may then be attached thereto.

In certain embodiments, forming the end of the stop valve, into which the one-way valve is to be fitted, may be with a recess and fitting the one-way valve to that end of the stop valve so that a periphery of the one-way valve seats in that recess.

The method described above may further include configuring the recess so that the one-way valve is fully counter sunk into the end of the stop valve with an end surface of the one-way valve flush with an end surface of the stop valve. Additionally or alternatively, the step of forming the one-way valve and the stop valve as parts of a single piece of elastomeric material may include cutting respective slits in each part, namely each valve.

In certain embodiments, after attaching the body parts together, automated function testing by applying compressed air followed by suction pressure from either end of the connector may be carried out. Additionally or alternatively, as may checking for predetermined flow rate upon the application of compressed air and checking for maintained pressure upon application of suction pressure.

BRIEF DESCRIPTION OF THE DRAWINGS

The invention will be described further with reference to the accompanying drawings, in which:

FIG. 1 is an exploded cross-sectional view of a prior art medical sampling connector;

FIG. 2 is a corresponding cross-section of the assembled prior art connector of FIG. 1;

FIG. 3 is an end view of the assembled prior art connector at the right hand end in FIG. 2;

FIG. 4 is a side view of the conjoined valve parts, as initially fabricated, which form part of preferred practical embodiments of the medical connector according to the present invention;

FIGS. 5 and 6 are respective end views of the conjoined valve parts shown in FIG. 4;

FIGS. 7 and 8 are respective further side views of the conjoined valve parts of FIG. 4, as viewed from left and right respectively in FIG. 4;

FIGS. 9 to 12 are longitudinal cross-sections through the conjoined valve parts of FIGS. 4 to 8 showing the sequence of folding and interconnection of the respective valve portions;

FIG. 13 is a cross-section along line A-A in FIG. 9 of the one-way valve part;

FIGS. 14 to 17 are exploded cross-sectional views showing the sequence of assembly of the conjoined valve parts with the connector body in a first preferred practical embodiment of medical connector according to the present invention, FIG. 16 being a cross-section in a plane at 90° compared to FIG. 15 and FIG. 17 being in the same plane as FIG. 16;

FIG. 18 is a cross-sectional view, same orientation as FIGS. 16 and 17, of the fully assembled connector;

FIGS. 19 to 21 are perspective views of the sequence of assembly of the same connector, corresponding to FIGS. 14, 15 and 18;

FIG. 22 is a perspective view showing the fully assembled connector, as in FIG. 21, but from the opposite direction;

FIGS. 23 and 24 are cross-sectional views, corresponding to FIGS. 15 and 18, showing a medical connector, not within the scope of the present invention, which does not include a one-way valve, but can be readily produced by use of same moulded parts of the connector of the invention as shown in FIGS. 14 to 22;

FIG. 25 is a plan view of a second preferred practical embodiment of a medical connector according to the present invention in which the connector body is a one-piece body with hinged closure, shown in initial open condition of the connector body;

FIG. 26 is a cross-section of the same, second embodiment along line B-B in FIG. 25;

FIG. 27 is a side view of the connector shown in FIG. 25 with the connector body partially closed;

FIG. 28 is an end view of the same connector from the right hand end of FIG. 27; and FIGS. 29 and 30 are corresponding side and end views of the fully assembled connector of the second embodiment, namely with the connector body closed around the valves.

DETAILED DESCRIPTION

A medical sampling connector which has been trialled publicly by the applicant is shown in FIGS. 1 to 3. This comprises a body 10, formed by an outer body sleeve 11 and an inner body sleeve 12, and inside the body 10 there is mounted a one-way valve 18 and a stop valve 16. As best shown in FIG. 2, the one-way valve is mounted between the outer body sleeve 11 and the inner body sleeve 12, while the stop valve 16 is separately mounted inside the distal end of the inner body sleeve 12.

The outer body sleeve 11 is provided at a first end with a male Luer lock connector portion 13 which, in use, is designed to fit to a sampling port of a known three-way tap for arterial blood sampling. The inner body sleeve 12 fits into the opposing, second end of the outer body sleeve 11 and projects a distance beyond the second end, as shown in FIG. 2. The inner body sleeve 12 is itself formed of two parts, namely a swabable closure portion 14 and a tubular extension 15, and it is the closure portion 14 which projects from the second end of the sleeve 11. Thus, the connector body 10 as a whole has a first end 25 and a second end 26 and provides a fluid flow passage from a first aperture at the first end 25 to a second aperture at the second end 26. The first end 25 is provided by the outer body sleeve 11 and the second end 26 is provided by the projecting closure portion 14 of the inner body sleeve 12.

Components 11, 14, 15 of the body 10 are moulded of known medical grade thermoplastic material and are substantially rigid.

The stop valve 16 which is mounted inside the inner body sleeve 12, primarily within the closure portion 14, is a known configuration of swabable entry valve 16 of elastomeric material, such as medical grade silicon rubber. The end of this valve 16 has an end wall which is flush with the free end 26 of the closure portion 14 and which is formed with a slit 17, as shown in FIG. 3. The swabable entry valve 16 is accommodated in the inner body sleeve 12, as shown. It extends only a short distance into the tubular extension 15, which is connected on to the closure portion 14, typically by welding or by adhesive and provides a rear valve seat for the valve 16. The swabable entry valve 16 acts as a stop valve in that it prevents fluid, specifically liquid, which enters the connector body 10 from the first end 25 leaking out of the second end 26, but allows liquid to flow from the first end 25 to the second end 26 and out through the second end when a further complementary connector portion engages with the closure portion 14 and opens the slit 17 by projecting there through. In this respect, the closure portion 14 carries external screw threads and the complementary connector portion will typically be a standardised male Luer lock connector portion, similar to that at the first end 25 of the connector body 10.

A component consisting of the inner body sleeve 12 with the swabable entry valve 16 mounted therein is a previously known commercially available component, widely used as a connector fitment on a bag of saline or other medical fluid for enabling quick connection of same to a Luer lock connector portion at one end of a patient fluid supply line.

The one-way valve 18 is in the form of a duck bill valve, namely a body of elastomeric material having a circular disc base 19 and a tapered extension 20 from one side of the base which has a slit 21 through its pointed end. Fluid is therefore able to flow through this valve 18 from the direction of the base 19 and through the slit 21, but is not able to flow in the reverse direction because fluid at the outside of the tapered extension 20 exerts pressure on the outside of the extension to close the slit 21.

As shown in FIG. 2, the one-way valve 18 is mounted in the interior of the outer body sleeve 11, centrally in the flow path through the connector, just inside the male Luer lock connector portion 13, with the base 19 seated in an annular recess in the outer body sleeve 11 and the tapered portion 20 extending downstream in the direction of flow from the first to the second end of the body 10. The one-way valve 18 is retained in this position by the extension 15, which effectively acts as a spacer between the one-way valve 18 and the stop valve, namely the swabable entry valve 16.

Conforming to accepted colour coding within the UK health service, the outer body sleeve 11 is coloured red to show that the connector is a one-way connector appropriate for connection to arterial sampling lines so that blood can only flow one-way, out of the patient and no liquid can flow in.

The functioning of the one-way, arterial connector shown in FIGS. 1 to 3 has been found to be satisfactory, but assembly of this device is difficult, time-consuming and may not be totally reliable in sealing around the one-way valve 18.

The present invention addresses the need for more cost-effective and reliable assembly of such a medical use connector incorporating both a one-way valve and a stop valve.

FIGS. 5 to 22 illustrate a preferred practical embodiment of a connector in accordance with the present invention. This comprises a one-way valve 118 and a stop valve 116 which are formed, by moulding, as parts of a single piece of elastomeric material, as shown in FIGS. 5 to 12. These parts are hingedly connected by way of a short strap 115 of the elastomeric material. A suitable elastomeric material is medical grade silicon rubber.

The stop valve part 116 has a through bore 122 between a first end 123 and a second end 124. The bore 122 is closed at the first end 123 by an end wall provided with a slit 117. An annular recess 126 is formed at the second end 124 as an enlargement of the through bore 122. The strap 115 connecting to the one-way valve 118 is connected at this second end 124. As illustrated in the sequence from FIG. 9 to FIG. 12, an integrated one-way and stop valve is assembled by the one-way valve part 118 folding round and fitting into the recess 126. In this respect, the one-way valve part 118 is formed as a duck bill valve with a circular disc base 119 and a tapered extension 120 which has an elongate slit 121 at its pointed end, as indicated in FIG. 13. Accordingly, when the stop valve 118 is folded into position, the disc 119 fits snugly into the recess 126 to provide a fluid tight seal between these valve parts 118, 116, with the tapered portion 120 projecting into the bore 122. As shown, the base 119 of the one-way valve 118 is preferably fully counter sunk into the recess 126 in the end 124 of the stop valve part 116.

A shallow recess 127 is provided radially in the end surface of the stop valve at its second end 124 to accommodate the strap 115.

This integrated stop valve and one-way valve, shown in its final disposition in FIG. 12, also FIGS. 15 and 16, is therefore simple and cost-effective to manufacture in a single moulding. One or both of the slits 117, 121 may be formed by cutting the material from which the respective valve parts 116, 118 are made. It is also easy to assemble without any skill and, in a particularly reliable manner, the stop valve 118 will always be fitted in correct orientation directly into the end 124 of the one-way valve 116. Importantly also, a reliable fluid tight seal will be formed between these two valve parts 116, 118 between contacting surfaces of the disc 119 and the annular recess 126. Thus, this particular arrangement has the advantages both of economic production and of self-alignment of the two valve parts during assembly. The alignment results in reliability of sealing between the respective valve parts.

As shown in FIGS. 14 to 22, this particular practical embodiment of connector in accordance with the present invention has an outer body 100 formed of two parts 112, 114 only. The first part 112 provides a male Luer lock connector 113, with conventional male Luer tapered central projection surrounded by an internally threaded collar. The second part 114 serves as a housing for the integrated one-way and stop valve 116/118 and provides an externally threaded female end 111 to the connector body 100. The second part 114 has an annular projection 128 at its end opposite to the externally threaded portion 111, while the first part 112 has a corresponding annular groove 129 in its end facing away from the male Luer lock arrangement 113. The parts 112, 114 are accordingly connected together to form the outer body 100 by location of the projection 128 into the mating groove 129 and by use of adhesive or by means of ultrasonic welding, for example. These parts 112, 114 are suitably made from medical grade ABS or similar hard thermoplastics material. To comply with required convention for colour coding, the part 112 will be coloured red to signify that the connector incorporates a one-way valve, while the part 114 will be of substantially transparent material.

The assembly process of the connector is illustrated in FIGS. 14 to 18, by cross-sectional views, and correspondingly by FIGS. 19 to 22, isometric views. First of all the integrated one-way and stop valve 118, 116 is produced by folding over the one-way valve 118 to fit directly into the end 124 of the one-way valve 118, as previously described. This integrated valve is then located into the body part 114, as shown in FIG. 17 so that the end wall 123 of the valve part 116 is substantially flush with the threaded end 111 of the body part 114, and a substantial portion of the remainder of the cylindrical outer surface of the valve part 116 is in contact with the inner surface of the body part 114. The other body part 112 is then located onto the end of the body part 114 with the projection 128 locating in the groove 129 and being affixed in fluid tight manner by ultrasonic or radio-frequency welding process or by adhesive, as previously described, so that the inner, mating face of the body part 112 also seals against the end surface of the conjoined stop valve 116 and one-way valve 118.

After connecting the outer body parts 112, 114 together, automated testing of the fluid tight seal can be undertaken by applying compressed air followed by suction pressure from either end of the assembled connector, checking for predetermined flow rate upon the application of compressed air and checking for maintained pressure upon application of suction pressure.

The outer body part 114 and the stop valve part 116 mounted therein provide a swabable needleless access port comparable to that of the FIG. 2 embodiment of the prior art and other prior art medical connectors. This is necessary for the connector of the invention to be compatible with connector portions of existing medical devices, in this case conventional male Luer lock connector portions of sampling syringes since this embodiment of the connector of the invention will typically be used at the sampling port of a three-way tap for arterial blood sampling.

FIGS. 23 and 24 illustrate a two way connector which is not within the scope of the present invention. It demonstrates that a further advantage of the aforesaid connector of the invention is that the same parts can be used to manufacture a two way connector with stop valve simply by omitting the one-way valve part 118 from the moulding of elastomeric material, or cutting away this part in a simple additional cutting step in order to switch manufacture to the two way connector. The parts here are designated by the same reference numerals for the corresponding parts in FIGS. 14 to 18, but commencing 200 instead of 100. Also, because this version is a connector allowing fluid flow in both directions, then to conform to accepted colour coding within the UK health service, the outer body part 212 would be coloured white.

FIGS. 25 to 30 illustrate further practical embodiments in accordance with aspects of the present invention. As shown, an integrated one-way and stop valve 118, 116 is provided which may be identical to that in the preceding FIGS. 5 to 12. However, in contrast to the preceding embodiment of FIGS. 14 to 22, the connector body 300 in which the integrated valve 118, 116 of elastomeric material is mounted is formed in one piece with a folding, snap fit closure 312. In other respects, the final external form of the outer body 300 is the same as that of the connector body 100 shown it in FIGS. 21 and 22, namely with a male Luer lock connector 313 at one end and with external screw threads 311 on a female connector portion at the opposite end. So long as the dimensions of the exterior of the stop valve part 116 and the body 300 are accurately matched so as to provide circumferential sealing inside the externally threaded portion 311 and also between the end 124 of the valve and the facing surface in the housing, this configuration of connector body 300 has the added advantage of eliminating the need for any additional welding of parts or use of adhesive, therefore further simplifying and reducing the cost of the manufacturing process of the overall connector.

However, in a further embodiment, only slightly modified relative to FIGS. 25 to 30, and in accordance with a further aspect of the invention, only a stop valve 116 may be provided within the one-piece connector body 300 with the folding, snap fit closure 312. In such embodiment, the one-way valve 118 will simply not be present and compared to the conjoined valve parts shown in FIGS. 4 to 12, it can simply be cut away, leaving only the stop valve 116. Since the stop valve 116 provides the entire elastomeric material valve exterior having dimensions matched to be a close fit inside the housing 300, the same advantages accrue here of assembly of only two parts, namely an outer body and a valve inside, and that additional steps of welding or use of adhesive in securing the housing by folding over and snap fitting the closure 312 may be unnecessary.

The invention is not restricted to the specific design details of any foregoing embodiments. For example, in other embodiments, the form of the strap 115 and the recess 126 in the one-piece moulding of the valves may be different to those in the illustrated embodiment. Indeed, these parts may be dispensed with in less favourable embodiments where reliability of sealing between the valve parts is not paramount. Also, in other embodiments the form of the one-way valve 18 may differ: it may not be a duck bill style of valve. Other variations in design detail are possible within the scope of the claims.

Throughout the description and claims of this specification, the word "comprise" means "including but not limited to", and it is not intended to (and does not) exclude other components.

Features described in conjunction with a particular embodiment of the invention are to be understood to be applicable to any other embodiment described herein unless incompatible therewith.

The invention claimed is:

1. A medical connector comprising a connector body having first and second apertures in fluid communication via a fluid flow conduit, a one-way valve disposed in the connector body to allow fluid to flow from the first aperture, through the fluid flow conduit and out of the second aperture, but not to allow fluid to flow from the second aperture and through the fluid flow conduit to the first aperture, and a stop valve which prevents fluid flowing out of the second aperture of the connector body unless a complementary end of a separate device engages the second aperture and opens the stop valve, wherein inside the connector body, the one-way valve is fitted directly into an end of the stop valve in a manner providing a fluid tight seal between these valves; and
wherein the one-way valve and the stop valve are formed as parts of a single piece of elastomeric material, said valves being hingedly connected such that the one-way valve is folded over and fitted directly into the end of the stop valve.

2. The connector according to claim 1 wherein the end of the stop valve into which the one-way valve is fitted is formed with a recess and a periphery of the one-way valve seats in that recess.

3. The connector according to claim 2 wherein the recess is configured so that the one-way valve is fully counter sunk into the end of the stop valve.

4. The connector according to claim 1 wherein the one-way valve part and the stop valve part are additionally connected by a strap portion of the elastomeric material, said strap being folded over such that the one-way valve fits into the end of the stop valve.

5. The connector according to claim 1 wherein the one-way valve is a duck bill valve.

6. The connector according to claim 1 wherein the stop valve is a swabable entry port valve.

7. The connector according to claim 1 wherein the connector body is formed of only two body parts.

8. The connector according to claim 1 wherein the connector body is formed in one piece with a folding, snap fit closure.

9. The connector according to claim 1 wherein the first aperture is within a male end of the connector which is configured as a male Luer lock connector portion and the second aperture is within a female end of the connector which is configured as a female Luer lock connector portion and provides a swabable entry port for attachment of a complementary needleless device.

10. A three-way tap arterial blood sampling device incorporating the sampling connector according to claim 1.

* * * * *